(12) United States Patent
Gasiot et al.

(10) Patent No.: US 11,730,433 B2
(45) Date of Patent: Aug. 22, 2023

(54) X-RAY DETECTOR

(71) Applicants: STMicroelectronics (Crolles 2) SAS, Crolles (FR); STMicroelectronics SA, Montrouge (FR)

(72) Inventors: Gilles Gasiot, Seyssinet-Pariset (FR); Severin Trochut, Crets en Belledonne (FR); Olivier Le Neel, Saint Martin d Uriage (FR); Victor Malherbe, Grenoble (FR)

(73) Assignees: STMicroelectronics (Crolles 2) SAS, Crolles (FR); STMicroelectronics SA, Montrouge (FR)

( * ) Notice: Subject to any disclaimer, the term of this patent is extended or adjusted under 35 U.S.C. 154(b) by 0 days.

(21) Appl. No.: 17/529,543

(22) Filed: Nov. 18, 2021

(65) Prior Publication Data

US 2022/0160314 A1 May 26, 2022

(30) Foreign Application Priority Data

Nov. 20, 2020 (FR) ...................................... 2011963

(51) Int. Cl.
*A61B 6/00* (2006.01)
*G01T 1/24* (2006.01)

(52) U.S. Cl.
CPC .............. *A61B 6/4208* (2013.01); *G01T 1/24* (2013.01)

(58) Field of Classification Search
CPC .................................................... A61B 6/4208
See application file for complete search history.

(56) References Cited

U.S. PATENT DOCUMENTS

| | | | | |
|---|---|---|---|---|
| 2009/0050814 | A1* | 2/2009 | Seefeldt | G01T 1/026 438/57 |
| 2013/0334897 | A1* | 12/2013 | Baumann | G11C 7/24 307/116 |

FOREIGN PATENT DOCUMENTS

| | | |
|---|---|---|
| GB | 2107860 A | 5/1983 |
| JP | S60158372 A | 8/1985 |
| WO | 0209775 A2 | 2/2002 |

OTHER PUBLICATIONS

INPI Search Report and Written Opinion for priority application, FR 2011963, report dated Oct. 28, 2021 (9 pages).

* cited by examiner

*Primary Examiner* — Hugh Maupin
(74) *Attorney, Agent, or Firm* — Crowe & Dunlevy

(57) ABSTRACT

An X-ray detector includes a first circuit with an NPN-type bipolar transistor and a second circuit configured to compare a voltage at a terminal of the NPN-type bipolar transistor with a reference value substantially equal to a value of the terminal voltage which would occur when the first circuit has been exposed to a threshold quantity of X-rays.

34 Claims, 4 Drawing Sheets

X-RAY DETECTOR

PRIORITY

This application claims the priority benefit of French Application for Patent No. 2011963, filed on Nov. 20, 2020, the content of which is hereby incorporated by reference in its entirety to the maximum extent allowable by law.

TECHNICAL FIELD

The present description generally concerns electronic devices and more particularly devices comprising an X-ray detection circuit.

BACKGROUND

X-rays are a form of high-frequency electromagnetic radiation formed of photons having an energy varying from some hundred eV (electron-volts), to several MeV.

X-rays may have a negative impact on the operation of electronic devices. For this purpose, electronic device manufacturers often advise against submitting the devices, for example, cells phones, to high quantities of X-rays. The warranty of these electronic devices generally does not include the damage caused by X-rays. There is a need to detect the application of X-rays to a device.

SUMMARY

An embodiment overcomes all or part of the disadvantages of known X-ray detectors.

An embodiment provides an X-ray detector comprising: a first electronic circuit comprising a first NPN-type bipolar transistor; and a second circuit configured to compare a voltage of the first electronic circuit with a reference value substantially equal to a value of said voltage which would occur when the first electronic circuit has received a threshold quantity of X-rays.

Another embodiment provides an X-ray detection method comprising comparing a voltage of a first electronic circuit comprising a first NPN-type bipolar transistor with a reference value substantially equal to a value of said voltage which would occur when the first electronic circuit has received a threshold quantity of X-rays.

According to an embodiment, said voltage is the voltage on one of the terminals of the first NPN-type bipolar transistor.

According to an embodiment, said voltage is the voltage on the emitter of the first NPN-type bipolar transistor.

According to an embodiment, said voltage is substantially constant during the operation of the device in the absence of X-rays.

According to an embodiment, the threshold quantity of X-rays is 10 grays.

According to an embodiment, the first circuit is configured so that the voltage on the base of the first NPN-type bipolar transistor is, during the operation of the detector, within a range of values for which the gain difference between the first NPN-type bipolar transistor having received no X-rays and the first NPN-type bipolar transistor having received the threshold quantity of X-rays is greater than 10.

According to an embodiment, the first circuit is configured so that the base voltage of the first NPN-type bipolar transistor is, during the operation of the detector, within a range of values for which the gain of the first NPN-type bipolar transistor having received no X-rays is at least 1.5 time greater than the gain of the first NPN-type bipolar transistor having received the threshold quantity of X-rays.

According to an embodiment, the first circuit comprises two branches, a first branch comprising a first transistor and the first NPN-type bipolar transistor coupled in series, and a second branch comprising second transistor and a second NPN-type bipolar transistor coupled in series, the first and second transistors being coupled as a current mirror so that the currents crossing the first and second NPN-type bipolar transistors are substantially equal.

According to an embodiment, the bases of the first and second NPN-type bipolar transistors are coupled by a resistor.

According to an embodiment, the base of each of the first and second NPN-type bipolar transistors is coupled to a node of application of a reference voltage by a resistor.

According to an embodiment, the collector of the second NPN-type bipolar transistor is coupled to the base of said first NPN-type bipolar transistor.

According to an embodiment, the detector comprises a circuit for generating the reference value comprising a third transistor is series with at least one resistor and at least one capacitor.

According to an embodiment, the third transistor is coupled as a current mirror with at least one of the first and second transistors.

BRIEF DESCRIPTION OF THE DRAWINGS

The foregoing features and advantages, as well as others, will be described in detail in the following description of specific embodiments given by way of illustration and not limitation with reference to the accompanying drawings, in which.

DETAILED DESCRIPTION

Like features have been designated by like references in the various figures. In particular, the structural and/or functional features that are common among the various embodiments may have the same references and may dispose identical structural, dimensional and material properties.

For the sake of clarity, only the steps and elements that are useful for an understanding of the embodiments described herein have been illustrated and described in detail.

Unless indicated otherwise, when reference is made to two elements connected together, this signifies a direct connection without any intermediate elements other than conductors, and when reference is made to two elements coupled together, this signifies that these two elements can be connected or they can be coupled via one or more other elements.

In the following disclosure, unless otherwise specified, when reference is made to absolute positional qualifiers, such as the terms "front", "back", "top", "bottom", "left", "right", etc., or to relative positional qualifiers, such as the terms "above", "below", "upper", "lower", etc., or to qualifiers of orientation, such as "horizontal", "vertical", etc., reference is made to the orientation shown in the figures.

Unless specified otherwise, the expressions "around", "approximately", "substantially" and "in the order of" signify within 10%, and preferably within 5%.

Figure 1:
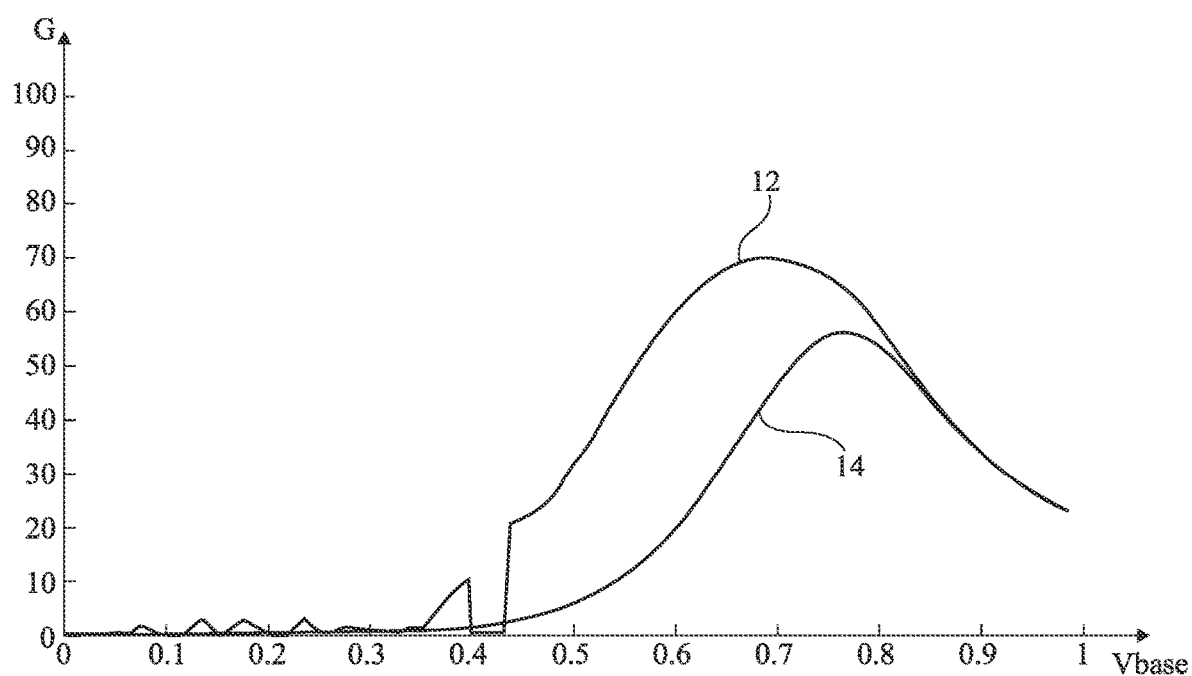
FIG. 1 illustrates the impact of X-rays on an NPN-type bipolar transistor.

FIG. 1 illustrates the impact of X-rays on an NPN-type bipolar transistor. More particularly, FIG. 1 is a graph showing the gain G of an NPN-type bipolar transistor according to the voltage Vbase on the transistor base.

The considered transistor is an NPN bipolar transistor, that is, a transistor comprising two PN junctions. The considered transistor comprises: a junction between a first N-type semiconductor region, forming the emitter, and a P-channel semiconductor region, forming the base, and a junction between the P-channel semiconductor region and a second N-type semiconductor region, forming the collector.

The values in the abscissa, that is, the values of voltage Vbase, thus correspond to the voltage on the P-channel semiconductor region. The values in the ordinate, that is, the values of gain G, correspond to the ratio of the collector current divided by the current of the base according to the value of base voltage Vbase.

During the obtaining of the gain values G, the emitter and the collector of the transistor are preferably coupled between two nodes of application of a power supply voltage. Preferably, the emitter is coupled, preferably connected, to a node of application of a reference voltage, for example, the ground, and the collector is coupled, preferably connected, to a node of application of the power supply voltage.

FIG. 1 comprises a curve 12 corresponding to the NPN-type bipolar transistor which has not been submitted to X-rays, for example, the transistor directly supplied by a manufacturer. The transistor has been submitted to a quantity of X-rays smaller than a threshold dose or quantity, to less than 1 gray, preferably to less than 0.1 gray.

FIG. 1 further comprises a curve 14 corresponding to the NPN-type bipolar transistor having been submitted to X-rays. The transistors corresponding to curves 12 and 14 are substantially identical, preferably are the same transistor. Curve 14 more precisely corresponds to the NPN-type bipolar transistor having been submitted to a quantity of X-rays greater than the threshold dose, for example, greater than 1 gray.

It can be observed that there exists a range D of values for Vbase, for example between 0.45 V and 0.7 V, where there is a significant difference between the values of the gain of the two curves. More particularly, for values of Vbase within range D, the values of curve 12 are significantly greater than the values of curve 14. For values of Vbase within range D, the values of curve 12 are greater than the values of curve 14 by at least a value 20.

Thus, for a voltage Vbase in the range from 0.45 to 0.7, the gain of curve 12 is greater than the gain of curve 14 by a factor greater than 1.5.

More generally, the inventors have observed that NPN transistors having been submitted to a quantity of X-rays greater than the threshold dose comprise a range of voltage values Vbase where the gain is at least two times, preferably at least three times, smaller than the gain of the identical transistor. The gain difference in the range of voltage values is preferably at least equal to a value of 10.

The inventors have also observed that the higher the quantity of X-rays, the greater the gain difference with respect to the same transistor before it is submitted to the X-rays, that is, the difference with respect to curve 12 for the transistor considered in FIG. 1. The gain variation is thus monotonous.

Figure 2:
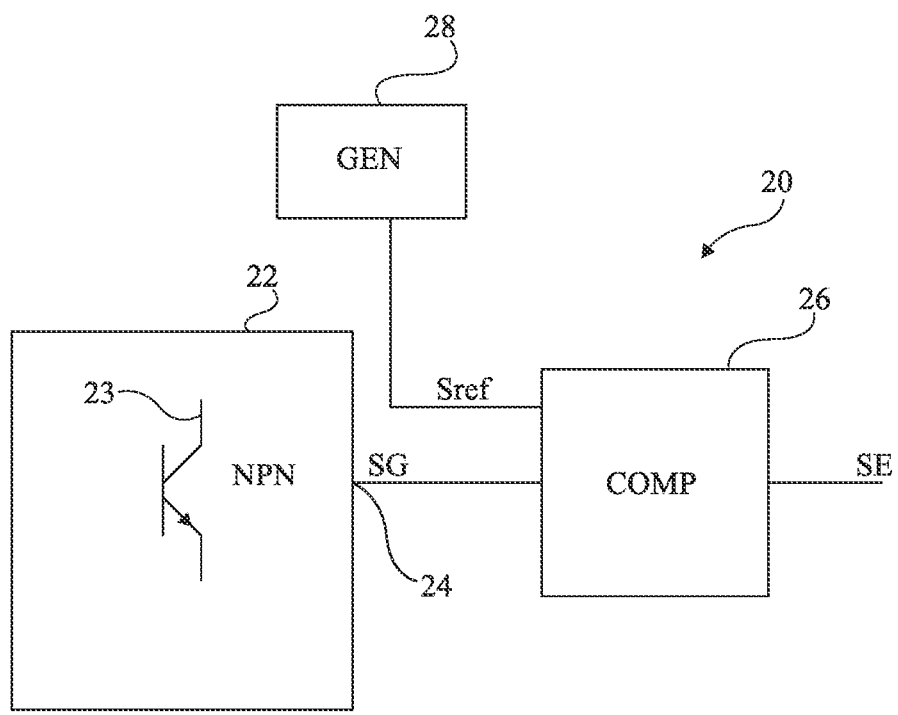
FIG. 2 schematically shows in the form of blocks an embodiment of an X-ray detector.

FIG. 2 schematically shows in the form of blocks an embodiment of an X-ray detector 20.

Detector 20 is intended to determine whether the device having the detector located therein has been submitted to a significant quantity, that is, a quantity greater than the threshold quantity, of X-rays since its manufacturing, for example, since the device has been sold. A significant quantity of X-rays for example means greater than 1 gray, preferably greater than 10 grays, preferably in the range from 10 to 50 grays. In other words, the threshold quantity is for example equal to 1 gray or to 10 grays.

Detector 20 comprises a circuit 22 (NPN). Circuit 22 comprises at least one NPN-type bipolar transistor 23, for example, a single NPN-type bipolar transistor. Transistor 23 is, for example, such as the NPN-type bipolar transistor described in relation with FIG. 1.

Circuit 22 is, for example, configured so that the base voltage of transistor 23 is, during the detector operation, within a range of values for which the gain difference between the transistor which has not received X-rays and the transistors having received the threshold quantity of X-rays, is preferably greater than 10, preferably greater than 20. Preferably, circuit 22 is configured so that the base voltage of transistor 23 is, during the detector operation, within a range of values for which the transistor gain having not received X-rays is at least 1.5 time greater, preferably at least three times greater, than the gain of the transistor having received the threshold quantity of X-rays.

Circuit 22 comprises an output node 24 having an output signal SG of circuit 22 delivered thereon. Signal SG is, for example, a voltage. Signal SG is representative of the gain of an NPN bipolar transistor 23 or more particularly of the impact of X-rays on transistor 23.

Node 24 is coupled, preferably connected, to one of the terminals of transistor 23. In other words, node 24 is coupled, preferably connected, to the collector or to the emitter of transistor 23, preferably to the emitter. The value of output signal SG is thus dependent on the value of the gain of transistor 23.

Preferably, circuit 22 is configured so that the value of output signal SG is substantially constant, in particular during the device operation. In other words, circuit 22 is configured so that the value of output signal SG is substantially constant in the absence of a variation of the gain of transistor 23.

Thus, when the device is submitted to a significant quantity of X-rays, the gain of transistor 23 is modified as described in relation with FIG. 1 and the value of output signal SG is also significantly modified. The variations of output signal SG are thus representative of the quantity of X-rays to which the device has been submitted.

The gain variation of the transistor when it is submitted to X-rays is monotonous. Similarly, the variation of signal SG is monotonous. More precisely, circuit 22 is configured so that signal SG is substantially constant when the transistor receives no X-rays and varies monotonously when the transistor receives X-rays. Thus, the greater the quantity of X-rays, the more signal SG varies monotonously. According to the circuit 22, the value of signal SG increases or decreases when the transistor is submitted to X-rays. For example, the greater the quantity of X-rays, the more signal SG increases. For example, the greater the quantity of X-rays, the more signal SG decreases.

Detector 20 comprises a comparison circuit 26 (COMP). Circuit 26 is configured to determine, from signal SG, whether the device has received a significant quantity of X-rays, in other words whether the gain of transistor 23 has been modified in a way representative of a significant quantity of X-rays received by the device.

Comparison circuit 26 is configured to compare signal SG with a threshold Sref. Threshold Sref is, for example, a voltage. Threshold Sref is generated by a voltage generator circuit 28 (GEN). Circuit 28 is configured to generate constant signal Sref in such a way that threshold Sref is representative of a threshold of X-rays received by transistor 23. More precisely, threshold Sref is representative of the threshold of received X-rays from which the change is desired to be detected, for example, from which is it considered that the device is damaged, for example from which it is considered that the device has received a quantity greater than the quantity of X-rays authorized or recommended by the manufacturer. Threshold Sref is substantially equal to the value of signal SG when the transistor has received this quantity of X-rays.

For example, if signal SG increases when the device receives X-rays, threshold Sref is greater than the constant value of signal SG, that is, the value of signal SG when the device has received no X-rays. Similarly, if signal SG decreases when the device receives X-rays, threshold Sref is smaller than the constant value of signal SG, that is, the value of signal SG when the device has not received X-rays.

Circuit 26 is configured to deliver an output signal SE representative of the comparison between signal SG and threshold Sref. Preferably, signal SE takes a first value if signal SG is smaller than threshold Sref and a second value if signal SG is greater than threshold Sref. If circuit 22 is configured so that the value of signal SG increases when the device receives X-rays, the first value of signal SE corresponds to a quantity of X-rays smaller than the threshold, and the second value of signal SE indicates that the X-ray threshold has been exceeded. Similarly, if circuit 22 is configured so that the value of signal SG decreases when the device receives X-rays, the second value of signal SE corresponds to a quantity of X-rays smaller than the threshold, and the first value of signal SE indicates that the X-ray threshold has been exceeded.

Figure 3:
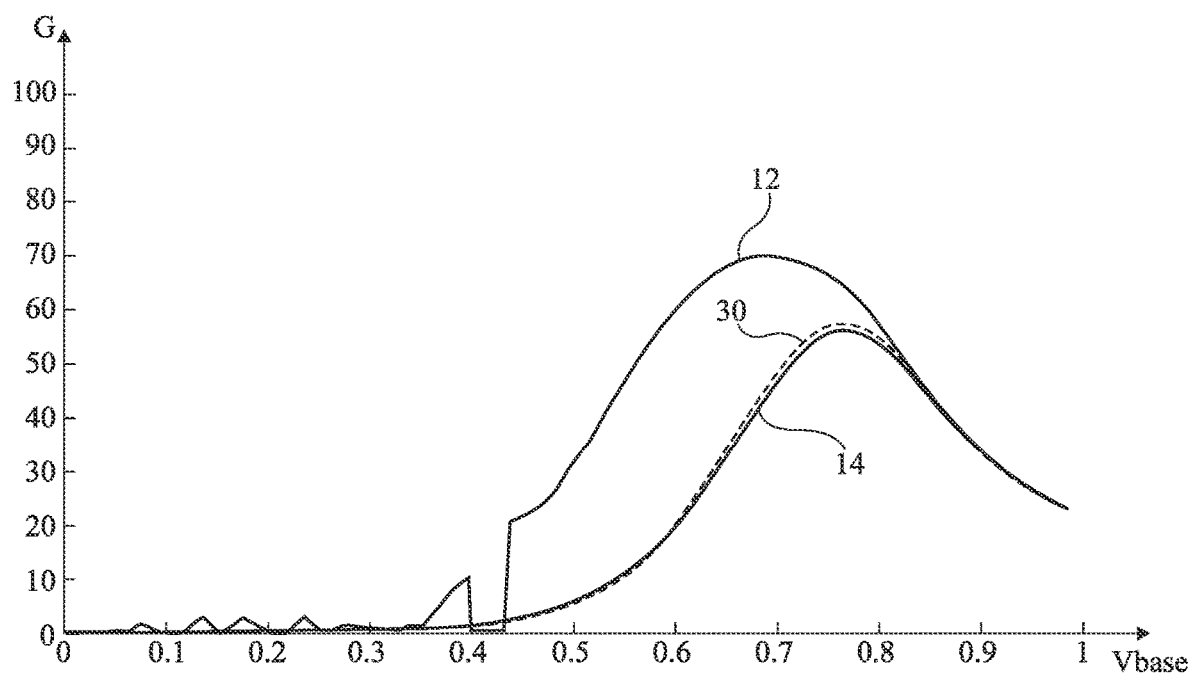
FIG. 3 shows the impact of X-rays on an NPN-type bipolar transistor after several days.

FIG. 3 shows the impact of X-rays on an NPN-type bipolar transistor after several days. More precisely, FIG. 3 is a graph showing, like FIG. 1, the gain G of an NPN-type bipolar transistor according to the voltage Vbase on the transistor base.

FIG. 3 shows the curves 12 and 14 described in relation with FIG. 1. Curve 12 shows the gain for a transistor which has received no X-rays and curve 14 shows the gain of this same transistor after the transistor has received a quantity of X-rays, for example, equal to the threshold dose.

FIG. 3 further shows a curve 30. Curve 30 corresponds to the gain of the same transistor as curves 12 and 14 after several days, for example, five days, during which the transistor receives no X-rays.

It can be observed that the values of curves 14 and 30 are substantially equal. Thus, the gain of the transistor does not vary when the transistor receives no X-rays. In particular, the transistor gain does not recover its original values, that is, the values of curve 12. The gain variations of the transistor are thus durable.

It is thus possible to determine whether the device has received a significant quantity of X-rays several days after the end of the reception of X-rays. Thus, output signal SE, representative of the quantity of X-rays received in the past by the device, maintains the value indicating that the X-ray threshold is exceeded, preferably definitively. It is thus possible for a device external to the device comprising detector 20 to obtain the information according to which the device has received or not a quantity of X-rays greater than the threshold determined in the past.

Figure 4:
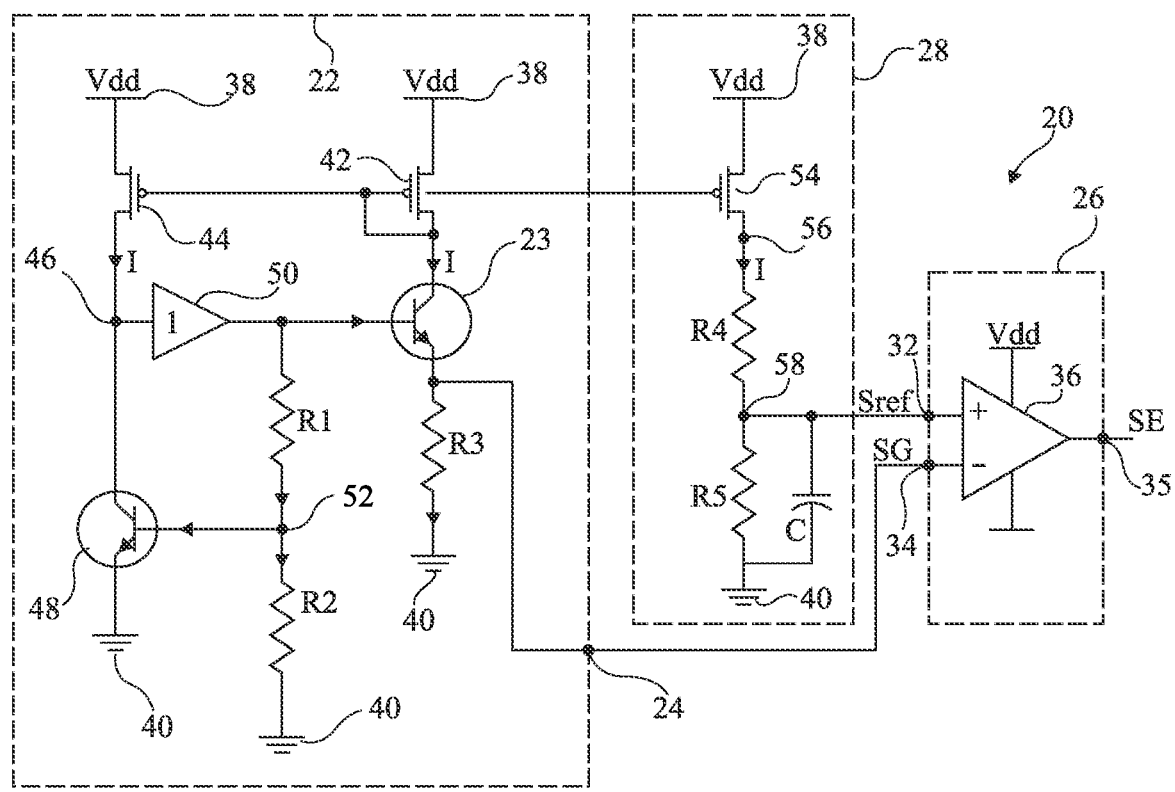
FIG. 4 shows in further detail an embodiment of an X-ray detector.

FIG. 4 shows in further detail an embodiment of an X-ray detector 20.

Detector 20 comprises comparison circuit 26. Circuit 26 receives, on an input 32, threshold Sref and, on an input 34, signal SG. Circuit 26 delivers, on an output 35, signal SE.

Circuit 26 comprises, in this example, a comparator 36. Comparator 36 is powered with a power supply voltage Vdd. Voltage Vdd is the power supply voltage of detector 20, for example, the power supply voltage of the device. Comparator 36, for example, comprises a non-inverting input coupled, preferably connected, to an input of circuit 26, preferably to input 32. Comparator 36, for example, comprises an inverting input coupled, preferably connected, to an input of circuit 26, preferably to input 34.

Detector 20 comprises circuit 22, generating signal SG. Circuit 22 comprises two NPN-type bipolar transistors. Circuit 22 comprises transistor 23. Transistor 23 is, as previously described, an NPN-type bipolar transistor. Transistor 23 is coupled, by its conduction terminals, between a node 38 of application of power supply voltage Vdd and a node 40 of application of a reference voltage, for example, the ground. Transistor 23 is coupled to node 40 by a resistor R3 and is coupled to node 38 by a transistor 42, for example, a P-channel metal oxide semiconductor field-effect transistor (MOSFET).

More particularly, the emitter of transistor 23 is coupled to node 40. A terminal of resistor R3 is thus coupled, preferably connected, to node 40 and another terminal of resistor R3 is coupled, preferably connected, to the emitter of transistor 23. The emitter of transistor 23 is coupled, preferably connected, to output node 24. The emitter of transistor 23 is thus coupled, preferably connected, to the input 34 of comparison circuit 26. Signal SG thus corresponds to the voltage on the emitter of transistor 23.

The collector of transistor 23 is coupled to node 38. More particularly, a conduction terminal of transistor 42, for example, the source, is coupled, preferably connected, to node 38 and the other conduction terminal of transistor 42, for example, the drain, is coupled, preferably connected, to the collector of transistor 23.

Transistor 42 is coupled as a current mirror with a transistor 44, for example, a P-channel MOSFET transistor, preferably a transistor identical to transistor 42. In other words, transistor 44 is coupled between node 38 and a node 46. More precisely, a conduction terminal of transistor 44, for example the source, is coupled, preferably connected, to node 38 and the other conduction terminal of transistor 44, for example, the drain, is coupled, preferably connected, to node 46. Further, the gate of transistor 44 is coupled, preferably connected, to the gate of transistor 42. Further, the gate of transistor 42 is coupled, preferably connected, to the conduction terminal of transistor 42 coupled, preferably connected, to transistor 23, for example, the drain of transistor 42.

Circuit 22 comprises a second NPN-type bipolar transistor 48. Transistor 48 is preferably identical to transistor 23. Transistor 48 is coupled between nodes 38 and 40. More particularly, the emitter of transistor 48 is coupled, preferably connected, to node 40. The collector of transistor 48 is coupled to node 38 by transistor 44. In other words, the collector of transistor 48 is coupled, preferably connected, to node 46. Thus, a same current I flows through transistors 23 and 48.

Circuit 22 thus comprises two branches, each branch comprising a first transistor 42, 44, for example, a P-channel MOSFET transistor, series-coupled with a second NPN-type bipolar transistor 23, 48. The first transistors are coupled as a current mirror. Thus, a same current I flows through the bipolar transistors.

Node 46 is coupled to the base of transistor 23, for example, by an amplification circuit 50. Circuit 50, for example, has a gain substantially equal to 1. The input of circuit 50 is coupled, preferably connected, to node 46 and the output of circuit 50 is coupled, preferably connected, to the base of transistor 23.

The base of transistor 23 is further coupled to node 40. The base of transistor 23 is, for example, coupled to node 40 by two resistors R1 and R2. More precisely, resistor R1 is coupled between the base of transistor 23 and a node 52. Resistor R2 is coupled between node 52 and node 40. In other words, a terminal of resistor R1 is coupled, preferably connected, to the base of transistor 23 and the other terminal of resistor R1 is coupled, preferably connected, to node 52. Further, a terminal of resistor R2 is coupled, preferably connected, to node 40 and the other terminal of resistor R2 is coupled, preferably connected, to node 52. Further, node 52 is coupled, preferably connected, to the base of transistor 48. In other words, the bases of transistors 23 and 48 are coupled by resistor R2. The base of transistor 52 is coupled to node 40 by resistor R2. The base of transistor 23 is coupled to node 40 by resistors R1 and R2 in series.

Resistors R1 and R2 are preferably selected in such a way that the base voltage of transistor 23, and for example, the base voltage of transistor 48, are within the previously-described range of values.

An advantage of the circuit 22 of FIG. 4 is that the voltage variations, in particular the variations of the voltage on the emitter of transistor 23, that is, the variations of signal SG, are substantially independent from temperature. Thus, the variations of signal SG, representative of the quantity of X-rays received by the device, are independent from the temperature of the device. Signal SG is thus substantially constant in the absence of X-rays.

Detector 20 further comprises circuit 28 which is configured for generating threshold Sref. Circuit 28 comprises a transistor 54, for example, a P-channel MOSFET transistor. Transistor 54 is, for example, series-coupled with an assembly comprising at least one resistor and at least one capacitor. Circuit 28 comprises, in the example of FIG. 4, two resistors R4 and R5. Transistor 54 and resistors R4 and R5 are series-coupled between node 38 and node 40.

Transistor 54 is coupled between node 38 and a node 56. More particularly, a conduction terminal of transistor 54, for example, the source, is coupled, preferably connected, to node 38 and the other conduction terminal, for example the drain, is coupled, preferably connected, to node 56. Transistor 54 is coupled as a current mirror with transistor 42. Thus, the gate of transistor 54 is coupled, preferably connected, to the gate of transistor 42.

Resistor R4 is coupled between node 56 and a node 58. In other words, a terminal of resistor R4 is coupled, preferably connected, to node 56 and the other terminal is coupled, preferably connected, to node 58. Resistor R5 is coupled between node 58 and node 40. In other words, a terminal of resistor R5 is coupled, preferably connected, to node 58 and the other terminal is coupled, preferably connected, to node 40.

Circuit 28 further comprises a capacitor C. Capacitor C is coupled in parallel with resistor R5. In other words, a terminal of capacitor C is coupled, preferably connected, to a terminal of resistor R5 and the other terminal of capacitor C is coupled, preferably connected, to the other terminal of resistor R5. In other words, one of the terminals of capacitor C is coupled, preferably connected, to node 58 and the other terminal of the capacitor is coupled, preferably connected, to node 40.

Threshold Sref corresponds to the voltage on node 58. The value of threshold Sref is dependent on the values of resistors R4 and R5 and on the capacitance of capacitor C. The values of resistors R4 and R5 and the capacitance of capacitor C are selected to obtain a value of Sref corresponding to the value of signal 24 when the device comprising the detector receives a quantity of X-rays equal to the threshold considered as acceptable.

An advantage of the described embodiments is that they enable to determine whether the device has received a quantity of X-rays greater than a threshold. In particular, the described embodiments enable to determine, after the reception of the X-rays has ended, whether the device has received a quantity of X-rays greater than a threshold. Indeed, the impact of the radiations on the transistor gain is permanent. The device thus enables to detect the cumulated quantity of irradiation received by the device.

Various embodiments and variants have been described. Those skilled in the art will understand that certain features of these various embodiments and variants may be combined, and other variants will occur to those skilled in the art.

Finally, the practical implementation of the described embodiments and variations is within the abilities of those skilled in the art based on the functional indications given hereabove.

The invention claimed is:

1. An X-ray detector, comprising:
   a first circuit comprising a first NPN-type bipolar transistor; and
   a second circuit configured to compare a voltage of the first circuit with a reference value substantially equal to a value of said voltage which would occur when the first circuit has received a threshold quantity of X-rays;
   wherein the first circuit is configured so that a base voltage of the first NPN-type bipolar transistor is, during the operation of the detector, within a range of values for which a gain of the first NPN-type bipolar transistor having received no X-rays is at least 1.5 times greater than the gain of the first NPN-type bipolar transistor having received the threshold quantity of X-rays.

2. The detector according to claim 1, wherein said voltage is a voltage at one of the terminals of the first NPN-type bipolar transistor.

3. The detector according to claim 2, wherein said one of the terminals is an emitter of the first NPN-type bipolar transistor.

4. The detector according to claim 1, wherein said voltage is substantially constant during the operation of the device in the absence of X-rays.

5. An X-ray detector, comprising:
   a first circuit comprising a first NPN-type bipolar transistor; and
   a second circuit configured to compare a voltage of the first circuit with a reference value substantially equal to a value of said voltage which would occur when the first circuit has received a threshold quantity of X-rays;
   wherein the threshold quantity of X-rays is 10 grays.

6. The detector according to claim 5, wherein said voltage is a voltage at one of the terminals of the first NPN-type bipolar transistor.

7. The detector according to claim 6, wherein said one of the terminals is an emitter of the first NPN-type bipolar transistor.

8. The detector according to claim 5, wherein said voltage is substantially constant during the operation of the device in the absence of X-rays.

9. An X-ray detector, comprising:
a first circuit comprising a first NPN-type bipolar transistor; and
a second circuit configured to compare a voltage of the first circuit with a reference value substantially equal to a value of said voltage which would occur when the first circuit has received a threshold quantity of X-rays;
wherein the first circuit is configured so that a voltage at a base of the first NPN-type bipolar transistor is, during the operation of the detector, within a range of values for which a gain difference between the first NPN-type bipolar transistor having received no X-rays and the first NPN-type bipolar transistor having received the threshold quantity of X-rays is greater than 10.

10. An X-ray detector, comprising:
a first circuit comprising two branches, a first branch comprising a first transistor and a first NPN-type bipolar transistor coupled in series, and a second branch comprising a second transistor and a second NPN-type bipolar transistor coupled in series, the first and second transistors being coupled as a current mirror so that the currents flowing through the first and second NPN-type bipolar transistors are substantially equal; and
a second circuit configured to compare a voltage of the first circuit with a reference value substantially equal to a value of said voltage which would occur when the first circuit has received a threshold quantity of X-rays.

11. The detector according to claim 10, wherein bases of the first and second NPN-type bipolar transistors are coupled by a resistor.

12. The detector according to claim 11, wherein the base of each of the first and second NPN-type bipolar transistors is coupled to a node of application of a reference voltage by a resistor.

13. The detector according to claim 10, wherein a collector of the second NPN-type bipolar transistor is coupled to the base of the first NPN-type bipolar transistor through a unity gain amplifier circuit.

14. The detector according to claim 10, wherein said voltage is a voltage at one of the terminals of the first NPN-type bipolar transistor.

15. The detector according to claim 14, wherein said one of the terminals is an emitter of the first NPN-type bipolar transistor.

16. The detector according to claim 10, wherein said voltage is substantially constant during the operation of the device in the absence of X-rays.

17. The detector according to claim 10, wherein the threshold quantity of X-rays is 10 grays.

18. An X-ray detector, comprising:
a first circuit comprising a first NPN-type bipolar transistor; and
a second circuit configured to compare a voltage of the first circuit with a reference value substantially equal to a value of said voltage which would occur when the first circuit has received a threshold quantity of X-rays; and
a voltage generator circuit configured to generate the reference value comprising a third transistor in series with at least one resistor and at least one capacitor.

19. The detector according to claim 18, further comprising a first transistor coupled in series with the first NPN-type bipolar transistor, and wherein the third transistor is coupled as a current mirror with the first transistor.

20. The detector according to claim 18, further comprising a second transistor and a second NPN-type bipolar transistor coupled in series, and wherein the third transistor is coupled as a current mirror with the second transistor.

21. The detector according to claim 18, wherein said voltage is a voltage at one of the terminals of the first NPN-type bipolar transistor.

22. The detector according to claim 21, wherein said one of the terminals is an emitter of the first NPN-type bipolar transistor.

23. The detector according to claim 18, wherein said voltage is substantially constant during the operation of the device in the absence of X-rays.

24. The detector according to claim 18, wherein the threshold quantity of X-rays is 10 grays.

25. An X-ray detection method, comprising:
comparing a voltage of a first electronic circuit comprising a first NPN-type bipolar transistor with a reference value;
wherein the reference value is substantially equal to a value of said voltage which would occur when the first electronic circuit has received a threshold quantity of X-rays;
generating an output signal indicative X-ray exposure if the comparison is satisfied; and
applying a base voltage to the first NPN-type bipolar transistor that is within a range of values for which a gain of the first NPN-type bipolar transistor having received no X-rays is at least 1.5 times greater than the gain of the first NPN-type bipolar transistor having received the threshold quantity of X-rays.

26. The method according to claim 25, wherein said voltage is a voltage on one of the terminals of the first NPN-type bipolar transistor.

27. The method according to claim 26, wherein said one of the terminals is an emitter of the first NPN-type bipolar transistor.

28. The method according to claim 26, wherein said voltage is substantially constant during the operation in the absence of X-rays.

29. The method according to claim 26, wherein the threshold quantity of X-rays is 10 grays.

30. An X-ray detection method, comprising:
comparing a voltage of a first electronic circuit comprising a first NPN-type bipolar transistor with a reference value;
wherein the reference value is substantially equal to a value of said voltage which would occur when the first electronic circuit has received a threshold quantity of X-rays; and
generating an output signal indicative X-ray exposure if the comparison is satisfied; and
applying a voltage at the base of the first NPN-type bipolar transistor that is within a range of values for which a gain difference between the first NPN-type bipolar transistor having received no X-rays and the first NPN-type bipolar transistor having received the threshold quantity of X-rays is greater than 10.

31. The method according to claim 30, wherein said voltage is a voltage on one of the terminals of the first NPN-type bipolar transistor.

32. The method according to claim 31, wherein said one of the terminals is an emitter of the first NPN-type bipolar transistor.

33. The method according to claim 31, wherein said voltage is substantially constant during the operation in the absence of X-rays.

34. The method according to claim 30, wherein the threshold quantity of X-rays is 10 grays.

* * * * *